United States Patent [19]
Cignarella et al.

[11] Patent Number: 6,127,362
[45] Date of Patent: Oct. 3, 2000

[54] 9,10-DIAZATRICYCLO[4,4,1,1$^{2,5}$] DECANE AND 2,7-DIAZATRICYCLO [4,4,0,0$^{3,8}$] DECANE DERIVATIVES HAVING ANALGESIC ACTIVITY

[75] Inventors: Giorgio Cignarella; Paola Vianello, both of Milan, Italy

[73] Assignee: Neuroscienze S.C.A.R.L., Cagliari, Italy

[21] Appl. No.: 09/403,287

[22] PCT Filed: Apr. 17, 1998

[86] PCT No.: PCT/EP98/02252

§ 371 Date: Dec. 2, 1999

§ 102(e) Date: Dec. 2, 1999

[87] PCT Pub. No.: WO98/47902

PCT Pub. Date: Oct. 29, 1998

[30] Foreign Application Priority Data

Apr. 22, 1997 [IT] Italy .................................. MI97A0938

[51] Int. Cl.$^7$ ........................ A61K 31/495; C07D 487/18
[52] U.S. Cl. ................. 514/211.12; 514/211.08; 514/211.11; 540/553; 540/556
[58] Field of Search ..................... 540/553, 556; 514/211.08, 211.11, 211.12

[56] References Cited

FOREIGN PATENT DOCUMENTS

95/23152  8/1995  WIPO .

OTHER PUBLICATIONS

Mascal et al. Tetrahedron Letters, 37(1) 131–4, only Abs is provided, 1996.

*Primary Examiner*—Mukund J. Shah
*Assistant Examiner*—Pavanaram K Sripada
*Attorney, Agent, or Firm*—Birch, Stewart, Kolasch & Birch, LLP

[57] ABSTRACT

9,10-DIAZATRICYCLO[4,4,1,1$^{2,5}$]DECANE (Ia) AND 2,7-DIAZATRICYCLO[4,4,0,0$^{3,8}$]DECANE (Ib) DERIVATIVES HAVING ANALGESIC ACTIVITY.

(Ia)

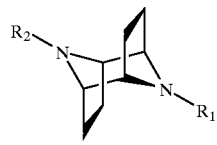

(Ib)

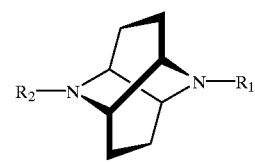

7 Claims, No Drawings

9,10-DIAZATRICYCLO[4,4,1,1$^{2,5}$] DECANE AND 2,7-DIAZATRICYCLO [4,4,0,0$^{3,8}$] DECANE DERIVATIVES HAVING ANALGESIC ACTIVITY

This application is a 371 of PCT/EP 98/02252 filed Apr. 4, 1998.

The present invention relates to 9,10-diazatricyclo [4.2.1.1$^{2,5}$]decane and 2,7-diazatricyclo[4,4,0,0$^{3,8}$]decane derivatives having analgesic activity.

WO 95/23152 and WO 94/16698 disclose 3,8-diazabicyclo[3.2.1]octane derivatives having central analgesic activity, wherein the two nitrogen atoms are respectively substituted with acyl groups and aryl or heteroaryl-acrylic groups. Said compounds proved to be particularly active as central analgesics and are characterized by satisfactory tolerability and poor or no induction of addiction and tolerance.

Now it has been found that analogues of two novel tricyclic systems, characterized by two endoethylenic bridges on the piperazine ring, have an even higher analgesic activity.

The compounds of the invention have the following general formulae:

Ia

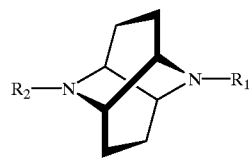
Ib in which $R_1$ and $R_2$ are both hydrogen or are different from each other, and are selected from hydrogen; $C_1$–$C_8$ alkyl; $C_2$–$C_{10}$ acyl; an Ar group wherein Ar is optionally substituted phenyl, optionally substituted naphthyl, an heterocyclic group containing 1 to 3 heteroatoms selected from oxygen, nitrogen and sulphur having 5 to 7 ring atoms, optionally benzofused and optionally substituted at the benzene ring; a group of formula —CH$_2$—CH═CH—Ar wherein Ar is as defined above.

Examples of Ar groups can be represented by the following formulae

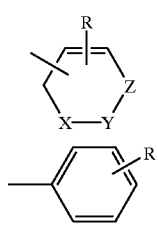

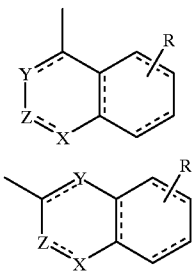

wherein X, Y and Z, which are the same or different, are selected from N, NH, S, O, ═(CH)$_n$ or —(CH$_2$)$_n$— wherein n=0–2 and R is hydrogen or a substituent selected from halogen atoms, nitro, amino, methoxy, ethoxy, $C_1$–$C_6$ alkylamino or $C_1$–$C_8$ acylamino groups.

Preferably, $R_1$ is a $C_2$–$C_{10}$ acyl group and $R_2$ is an Ar group or —CH$_2$—CH═CH—Ar as defined above.

A $C_2$–$C_{10}$ acyl group is preferably acetyl, propionyl or butyryl, more preferably propionyl.

$R_2$ is preferably a group of formula —CH$_2$—CH═CH—Ar wherein Ar is phenyl or substituted phenyl, more preferably phenyl.

The compounds of formulae I and Ib can be prepared according to the following schemes:

SCHEME 1

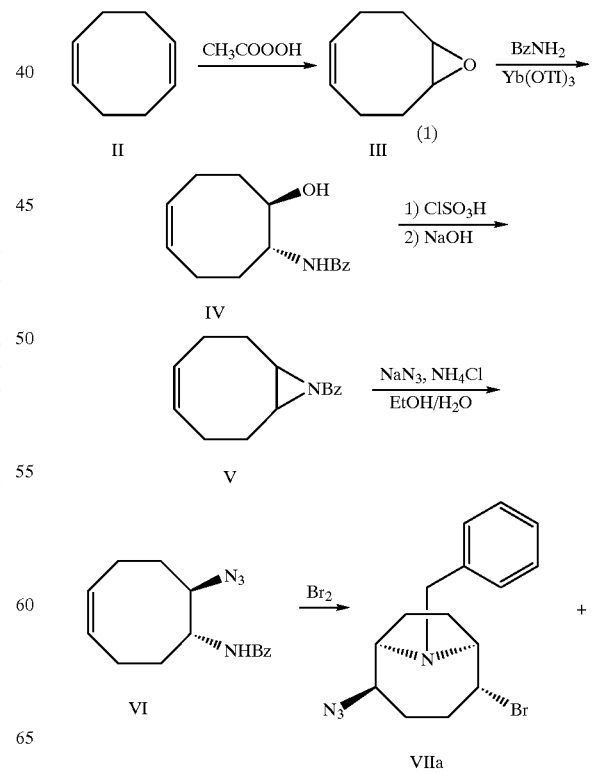

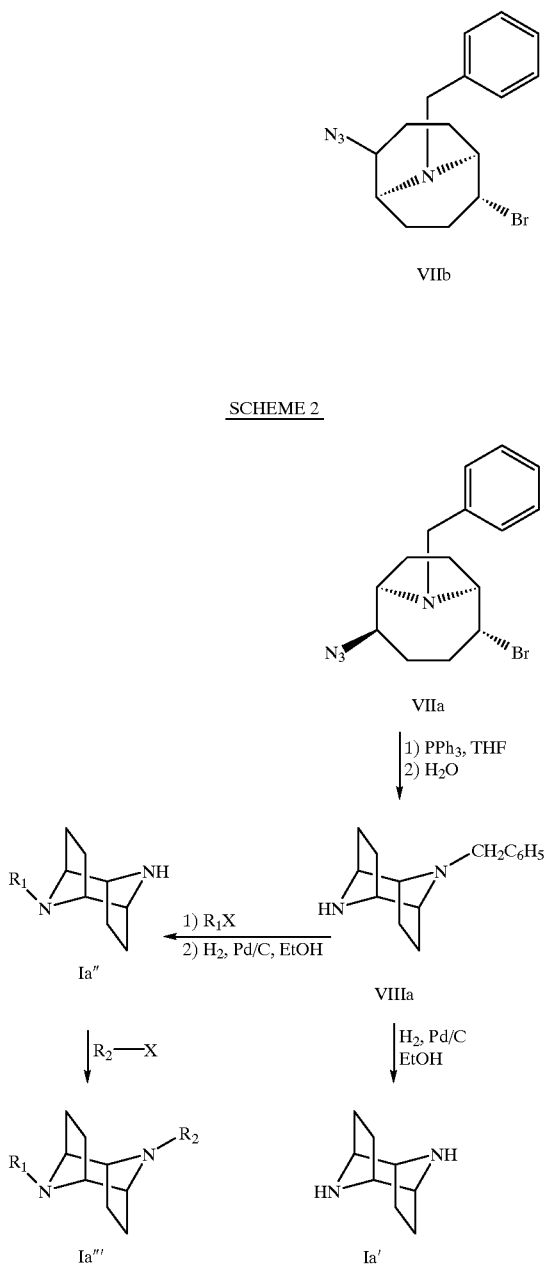

SCHEME 2

SCHEME 3

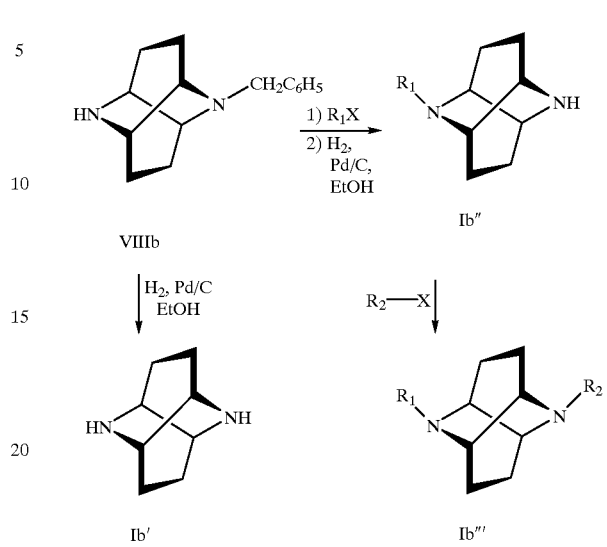

In the schemes reported above, X is a reactive group suitable for the desired N-alkylation or N-acylation reaction, for example a halogen atom, a mesyl, tosyl, acyl chloride, anhydride group and the like.

The process according to the invention comprises the reaction of 5,6-epoxycyclooctene III, easily obtainable from commercially available 1,5-cyclooctadiene II, with benzylamine in dichloromethane, in the presence of ytterbium (III) trifluoromethanesulfonate, to give aminoalcohol IV.

The alcohol group is then transformed into the corresponding sulphate ester which is refluxed in concentrated sodium hydroxide to yield aziridine V. The latter is treated with sodium azide and ammonium chloride with heating in ethanol and water to yield amino-azide VI, which is transformed into the compounds VIIa and VIIb by addition of bromine. The dibromo derivatives cannot be isolated as an intramolecular condensation occurs.

The compounds VIIa and VIIb are separated by chromatography according to conventional techniques.

The compounds VIIa and VIIb can then be converted into compounds of formula VIIIa or VIIIb, respectively, by treatment with triphenylphosphine in tetrahydrofuran and subsequent addition of water.

Conventional N-alkylation or N-acylation reactions, in suitable sequence, allow then to prepare the desired compounds.

The compounds of formula Ia and Ib have affinity to opioid receptors, evaluated according to the method described by Wood et al., Neuropharmacology, 1981, 20, 1219, which is up to 5-fold higher than that of the compounds described in WO 95/23152 and WO 94/16698.

The compounds of the invention, optionally in the form of pharmaceutically acceptable salts, can conventionally be formulated in pharmaceutical compositions suitable for the oral, parenteral or rectal administration. The daily dosage will, of course, depend on a number of factors, but it will generally range from 1 mg to 100 mg/day, optionally subdivided in more administrations.

The following example shows the invention in greater detail.

EXAMPLE

Trans-2-benzylamino-5-cyclooctene-1-ol (IV)

To a stirred solution of 5,6-epoxycyclooctene III (10.0 g, 0.081 mol) in dry $CH_2Cl_2$ (100 ml) kept under nitrogen atmosphere, benzylamine (10.35 g, 0.097 mol) and Ytterbium(III) trifluoromethanesulfonate (4.96 g, 0.008 mol) were added and the mixture was stirred for 24 hrs at room temperature. Extractive work-up of the reaction mixture with water and $CH_2Cl_2$ gave the title product as a white solid (yield 83%). m.p.: 70–71° C., b.p:140° C./1 mm Hg. $^1H$ NMR ($CDCl_3$): δ 7.59–7.56 (m, 2H, ArH), 7.38–7.35 (m, 3H, ArH), 5.64–5.44 (m, 2H, CH=CH), 5.42–5.00 (bs, $D_2O$ exchangeable, OH) 4.07 (AB syst, 2H, J=12.57 Hz, $PhCH_2$), 3.75–3.65 (m, 1H, CHOH), 3.00–3.15 (m, 1H, CHNH—), 2.35–2.02 (m, 6H), 1.95–1.42 (m, 2H).

Trans-2-benzylamino-5-cycloocten-1-ol sulphate ester

To a suspension of compound IV (2.6 g, 0.011 mol) in anhydrous ether (50 ml) kept under vigorous stirring at 0–5° C., chlorosulfonic acid (1.6 g, 0.011 mol) was added dropwise. The reaction mixture became gummy and difficult to stir. However, after stirring overnight at room temperature, the white solid that separated was filtered and washed with ether, yielding 3.2 g (93%) of the sulphate ester, m.p 162–163° C.

$^1H$ NMR ($CDCl_3$): δ 8.50–8.00 (bs $D_2O$ exchangeable, 1H, $^+NH$); 7.50–7.30 (m, 5H, ArH); 5.70–5.50 (m, 1H, CH=CH); 5.50–5.30 (m, 1H, CH=CH); 4.70–4.50 (m, 1H, $CHOSO_3^-$); 4.40–4.00 (m, 2H, $PhCH_2$); 3.50–3.30 (1H, CHN); 2.60–1.70 (m, 8H).

N-Benzyl-9-azabicyclo[6.1.0]-4-nonene (V)

The sulphate ester (4 g, 0.017 mol) was dissolved in a 33% sodium hydroxide solution (40 ml) and the mixture was refluxed for 2 hrs, cooled, saturated with potassium hydroxide and extracted with 3×50 ml ethyl acetate. The organic layers were collected, dried ($Na_2SO_4$) and the solvent evaporated to give the desired compound isolated by silica gel flash chromatography, eluting with $CH_2Cl_2$/Ethyl acetate 9:1 (yield 62%). B.p.:125° C./1 mm Hg.

$^1H$ NMR ($CDCl_3$): δ 7.39–7.15 (m, 5H, ArH), 5.64–5.45 (m, 2H CH=CH), 3.55 (s, 2H, $PhCH_2$), 2.50–2.25 (m, 2H, CHN) 2.20–1.90 (bm, 6H) 1.61–1.45 (m, 2H).

Trans-2-azido-1-benzylamino-5-cyclooctene

A solution of compound V (10 g, 0.047 mol), sodium azide (12.2 g, 0.19 mol), and ammonium chloride (10.02 g, 0.19 mol) in ethanol (500 ml) and water (100 ml) was refluxed for 4 hrs. Ethanol was evaporated off and the aqueous mixture was extracted with 3×150 ml $CH_2Cl_2$. The organic layers were collected, dried ($Na_2SO_4$) and the solvent evaporated to give the desired compound which was isolated as an oil by silica gel flash chromatography, eluting with $CH_2Cl_2$/Ethyl acetate 9:1 (yield 91%).

$^1H$ NMR ($CDCl_3$): δ 7.35–7.10 (5H, ArH), 5.60 (dq, 2H, J=5.5, CH=CH), 3.80 (AB syst, 2H, J=12.82, $PhCH_2$), 3.67 (dt, 1H, J=8.8, $CHN_3$); 3.00–2.75 (m, 1H, CHN); 2.60–2.30 (m, 2H); 2.25–2.00 (m, 4H); 1.90–1.60 (m, 2H).

2-β-Bromo-5-azido-9-benzyl-9-azabicyclo[4.2.1.]nonane (VIIa)

2-β-Bromo-6-azido-9-benzyl-9-azabicyclo[3.3.1.]nonane (VIIb)

To a solution of trans-2-azido-1-benzylamino-5-cyclooctene (2 g, 7.8 mmol) in cyclohexane (110 ml), stirred at 5° C. in subdued light, was slowly added a solution of 10% bromine in cyclohexane, until a yellow colour persisted in the reaction mixture. The solid which separated was filtered (1.6 g), treated with 10% sodium hydroxide and the bases thus liberated were extracted with ether. The organic layer was dried on $Na_2SO_4$ and the solvent evaporated. Flash chromatography on silica gel eluting with petroleum ether 40–60/diethyl ether 98:2 gave first compound VIIa as an oil (yield 23%), further elution gave compound VIIb as a white solid m.p. 75–76° C. (diethyl ether) (yield 19%).

VIIa: $^1H$ NMR ($CDCl_3$): δ 7.45–7.20 (m, 5H, ArH); 4.12 (t, 1H, J=7.2, CHBr); 3.90–3.70 (m, 3H, $PhCH_2$, CHN); 3.56 (q, 1H, J=4.8, $CHN_3$); 3.40–3.20 (m, 1H, CHN); 2.40–2.10 (m, 3H); 2.10–1.70 (m, 3H); 1.60–1.20 (m, 2H).

VIIb: $^1H$ NMR ($CDCl_3$): δ 7.45–7.20 (m, 5H, ArH); 4.50–4.30 (m, 1H, CHBr); 4.20–3.90 (m, 3H, $PhCH_2$, $CHN_3$); 3.20–3.00 (m, 1H, CHN); 3.00–2.90 (mn, 1H, CHN); 2.50–2.00 (m, 5H); 2.00–1.60 (m, 3H).

2-β-Bromo-5-iminophosphorane-9-benzyl-9-azabicyclo [4.2.1.]nonane

To a stirred solution of VIIa (0.4 g, 0.0012 mol) in dry tetrahydrofuran at room temperature, a stoichiometric amount of triphenylphosphine, dissolved in THF, was added dropwise, and the mixture was refluxed for 4 hrs, then cooled and added with HCl in diethyl ether. The resulting solid was filtered, treated with 20% $NaHCO_3$ and extracted with ethyl acetate. The organic layers were dried over $Na_2SO_4$ and the solvent was evaporated off. Flash chromatography eluting with diethyl ether/6 M $NH_3$ in methanol 95:5 gave the title compound in quantitative yields, m.p. 114–115° C.

9-Benzyl-9,10-diazatricyclo[4.2.1.1$^{2,5}$]decane (VIIIa)

A solution of the above compound (0.35 g, 0.6 mmol) in THF (9 ml) and water (0.1 ml) was refluxed for 15 hrs. After cooling, HCl was bubbled through the mixture, the resulting solid was decanted and separated from the liquid, the solvents and the excess HCl were removed by co-evaporation with ethanol. The title compound as hydrochloride was washed with diethyl ether and crystallised (MeOH/$Et_2O$) to give an 85% yield. m.p. (as free base) 75–76° C.

$^1H$ NMR ($CDCl_3$): δ 7.50–7.10 (m, 5H, ArH); 3.50 (s, 2H, $PhCH_2$), 3.20–3.00 (m, 2H, CHN); 2.90–2.70 (m, 2H, CHN); 2.20–2.00 (m, 2H); 1.90–1.70 (m, 4H); 1.60–1.40 (m, 2H). 9-Benzyl-2,7-diazatricyclo[4,4,0,0,$^{3,8}$]decane (VIIIb)

To a stirred solution of VIIb (10.3 g, 0.0031 mol) in anhydrous THF (30 ml) at room temperature, a stoichiometric amount of triphenylphosphine dissolved in THF was added and the mixture refluxed for 7 hrs. After cooling, water (0.1 ml) was added and the mixture refluxed overnight. The reaction was quenched as described for compound VIIIa. Flash chromatography eluting with diethyl/ ether/6M $NH_3$ in MeOH 95:7 gave the title compound (yield 56%). m.p. (as free base) 127–128° C.

$^1H$ NMR ($CDCl_3$): δ 7.50–7.10 (m, 5H, ArH); 3.90 (AB syst, 2H, J=13.7, $PhCH_2$), 3.20–3.00 (m, 2H, CHN); 2.80–2.60 (m, 2H, CHN); 2.30–1.50 (m, 8H).

9,10-Diazatricyclo[4.2.1.1$^{2,5}$]decane Ia'

2,7-Diazatricyclo[4,4,0,0,$^{3,8}$]decane Ib'

Compounds VIIIa and VIIIb hydrochlorides (0.14 g, 0.57 mmol) were dissolved in ethanol (6 ml). To this solution 10% w/w palladium on carbon was added together with a few μl of 6N hydrochloric acid. The mixture was hydrogenated at room temperature overnight, the catalyst was filtered off and washed with hot 50% ethanol in water. The filtrate was evaporated in vacuo to give the title compounds as hydrochlorides as white solids in quantitative yields.

Ia': m.p. 295° C. (EtOH/$H_2O$/$Et_2O$)

Ib': m.p. 300° C. (EtOH/$H_2O$/$Et_2O$).

$^1H$ NMR (DMSO): δ 8.80 (bs, $D_2O$ exchang., 2H, $^+NH.HCl$); 3.94 (app.s, 4H, CHN); 2.40–2.20 (m, 4H); 2.20–2.00 (m, 4H).

3.2HCl: m.p. 300° C. dec (EtOH/$H_2O$/$Et_2O$).

$^1H$ NMR ($D_2O$): δ 4.04 (app.d, 4H, CHN); 2.50–2.20 (m, 4H); 2.20–1.90 (m, 4H).

9-Propionyl-9,10-diazatricyclo[4.2.1.1.$^{2,5}$]decane 1a"

9-Propionyl-2,7-diazatricyclo[4,4,0,0$^{3,8}$]decane 1b″

A solution of propionic anhydride (6.9 mmol) in CH$_2$Cl$_2$ (2 ml) was added in one portion to an ice cooled solution of the appropriate benzyl derivative VIIIa or VIIIb (0.45 g, 1.9 mmol) in CH$_2$Cl$_2$ (15 ml). The mixture was refluxed for 1 h, allowed to cool to room temperature, alkalinized with a 40% sodium hydroxide excess and stirred overnight. Extraction with dichloromethane and drying yielded 9-propionyl-10-benzyl-derivatives (100%) which were hydrogenated as described above to give the title compounds as hydrochlorides (yield 96%).

Ia″: m.p. 230° C.
Ib″: m.p. 234° C.
9-Propionyl-10-cinnamyl-9,10-diazatricyclo[4.2.1.1.$^{2,5}$] decane Ia‴
2-Propionyl-7-cinnamyl-2,7-diazatricyclo[4,4,0,0$^{3,8}$]decane Ib‴

A mixture of the suitable propionyl derivative Ia″ or Ib″ (1.1 mmol), cinnamyl chloride (1.1 mmol), K$_2$CO$_3$ (1.1 mmol) in acetone was refluxed for 24 hrs. The inorganic salts were filtered off, the filtrate was evaporated and the residue purified by silica gel flash chromatography, eluting with petroleum ether 40–60/ethyl acetate. The title compounds were obtained in 85–95% yields.

Ia‴: m.p. 189–190° C.
Ib‴: m.p. 220–221° C.

Operating analogously to the procedure described above, using the suitable derivatives of m-chlorocinnamic, p-nitrocinnamic, 3-α-naphthyl-propionic acids, the following compounds were obtained:
9-propionyl-10-(m-chlorocinnamyl)-9,10-diazatticyclo [4.2.1.1$^{2,5}$]decane.HCl.H$_2$O; m.p.=90° C.,
9-propionyl-10-(p-nitrocinnamyl)-9,10-diazatricyclo [4.2.1.1$^{2,5}$]decane free base m.p.=132–133° C.,
9-propionyl-10-(3'α-naphthylpropenyl)-9,10-diazatricyclo [4.2.1.1$^{2,5}$]decane.HCl.2H$_2$O; m.p.=138–142° C.,
2-propionyl-7-(p-nitrocinnamyl)-2,7-diazatricyclo[4,4,0,0$^{3,8}$]decane.HCl.1/2H$_2$O; m.p.=135° C.

What is claimed is:

1. Compounds of formula (I):

Ia

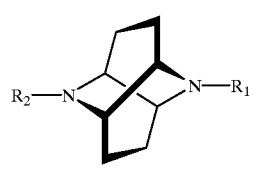

Ib wherein R$_1$ and R$_2$ are both hydrogen or are different from each other, and are selected from hydrogen; C$_1$–C$_8$ alkyl; C$_2$–C$_{10}$ acyl; an Ar group wherein Ar is optionally substituted phenyl, optionally substituted naphthyl, an heterocyclic group containing 1 to 3 heteroatoms selected from oxygen, nitrogen and sulphur having 5 to 7 ring atoms, optionally benzofused and optionally substituted at the benzene ring; a group of formula —CH$_2$—CH=CH—Ar wherein Ar is as defined above.

2. Compounds according to claim 1, wherein Ar groups are selected from

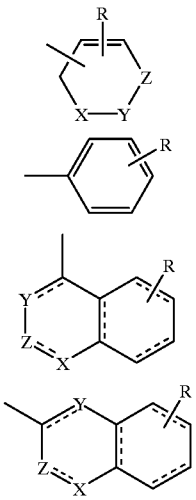

wherein X, Y and Z, which are the same or different, are selected from N, NH, S, O, =(CH)$_n$ or —(CH$_2$)$_n$— wherein n=0–2 and R is hydrogen or a substituent selected from halogen atoms, nitro, amino, methoxy, ethoxy, C$_1$–C$_6$ alkylamino or C$_1$–C$_8$ acylamino groups.

3. Compounds according to claim 1, wherein R$_1$ is a C$_2$–C$_{10}$ acyl group and R$_2$ is an Ar group or —CH$_2$—CH=CH—Ar as defined above.

4. Compounds according to claim 1 wherein the C$_2$–C$_{10}$ acyl group is acetyl, propionyl or butyryl.

5. Compounds according to claim 1 wherein R$_2$ is a group of formula —CH$_2$—CH=CH—Ar wherein Ar is phenyl or substituted phenyl.

6. Pharmaceutical compositions containing a compound of claim 1 as the active ingredient.

7. A method for relief of pain in an animal suffering from pain, comprising administering to said animal an analgesic effective amount of a compound of claim 1.

* * * * *